United States Patent
Russ et al.

(10) Patent No.: US 8,597,546 B2
(45) Date of Patent: Dec. 3, 2013

(54) PROCESS AND APPARATUS FOR PREPARING ACETYLENE AND SYNTHESIS GAS

(75) Inventors: Michael Russ, Roemerberg (DE); Dirk Grossschmidt, Mannheim (DE); Peter Renze, Mannheim (DE); Maximilian Vicari, Limburgerhof (DE); Horst Neuhauser, Dudenhofen (DE); Kai Rainer Ehrhardt, Speyer (DE); Christian Weichert, Bad Duerkheim (DE)

(73) Assignee: BASF SE, Ludwigshafen (DE)

( * ) Notice: Subject to any disclaimer, the term of this patent is extended or adjusted under 35 U.S.C. 154(b) by 37 days.

(21) Appl. No.: 13/292,691

(22) Filed: Nov. 9, 2011

(65) Prior Publication Data

US 2012/0119149 A1     May 17, 2012

Related U.S. Application Data

(60) Provisional application No. 61/412,406, filed on Nov. 11, 2010.

(51) Int. Cl.
*C01B 3/38* (2006.01)
*C01B 3/24* (2006.01)

(52) U.S. Cl.
USPC .......................................... 252/373; 423/650

(58) Field of Classification Search
USPC ....................................................... 252/373
See application file for complete search history.

(56) References Cited

U.S. PATENT DOCUMENTS

| 3,551,512 A | 12/1970 | Keckler et al. |
| 2011/0016790 A1 | 1/2011 | Grossschmidt et al. |
| 2011/0305605 A1 | 12/2011 | Jaeger et al. |

FOREIGN PATENT DOCUMENTS

| DE | 875 198 | 4/1953 |
| DE | 1 051 845 | 3/1959 |
| DE | 1 057 094 | 5/1959 |
| DE | 1 148 229 | 5/1963 |
| DE | 2 007 997 | 9/1970 |
| DE | 2 307 300 | 8/1973 |

(Continued)

OTHER PUBLICATIONS

"Ullmann's Encyclopedia of Industrial Chemistry", Fifth, Completely Revised Edition, vol. A1: Abrasives to Aluminum Oxide, 50 pages.

(Continued)

*Primary Examiner* — Melvin C Mayes
*Assistant Examiner* — Kenneth Vaden
(74) *Attorney, Agent, or Firm* — Oblon, Spivak, McClelland, Maier & Neustadt, L.L.P.

(57) ABSTRACT

The present invention provides a process for preparing acetylene and synthesis gas by partial oxidation of hydrocarbons with oxygen, by first separately preheating the starting gases comprising a hydrocarbon-containing stream and an oxygen-containing stream and then mixing them in a mixing zone and, after they have flowed through the burner block, reacting them in the firing space and then cooling the products rapidly, wherein the surface on the firing space side of the burner block is covered with a purge gas stream and this purge gas stream is introduced through the burner block by means of several bores, where the averaged ratio of effective surface area of the burner block to number of these bores in the burner block for the purge gas stream is within a range from 5 to 100 cm².

8 Claims, 2 Drawing Sheets

(56) References Cited

FOREIGN PATENT DOCUMENTS

| | | |
|---|---|---|
| DE | 39 04 330 A1 | 8/1990 |
| DE | 44 22 815 A1 | 1/1996 |
| GB | 824328 | 11/1959 |
| GB | 951100 | 3/1964 |
| GB | 1 414 684 | 11/1975 |
| GB | 1 482 975 | 8/1977 |
| WO | WO 2009/109473 A1 | 9/2009 |
| WO | WO 2010/097300 A1 | 9/2010 |
| WO | WO 2011/073123 A2 | 6/2011 |

OTHER PUBLICATIONS

U.S. Appl. No. 61/412,415, filed Nov. 11, 2010, Grossschmidt, et al.
U.S. Appl. No. 13/292,777, filed Nov. 9, 2011, Grossschmidt, et al.
U.S. Appl. No. 61/365,802, filed Jul. 20, 2010, Koenigsmann, et al.
U.S. Appl. No. 13/183,683, filed Jul. 15, 2011, Koenigsmann, et al.
U.S. Appl. No. 61/411,931, filed Nov. 10, 2010, Renze, et al.
U.S. Appl. No. 61/389,287, filed Oct. 4, 2010, Renze, et al.
U.S. Appl. No. 13/251,647, filed Oct. 3, 2011, Renze, et al.
International Search Report issued Jan. 27, 2012, in PCT/EP2011/068814, filed Oct. 27, 2011 (with English Translation of Category of Cited Documents).
U.S. Appl. No. 13/516,865, filed Jun. 18, 2012, Grossschmidt, et al.
U.S. Appl. No. 13/902,175, filed May 24, 2013, Vicari, et al.

PROCESS AND APPARATUS FOR PREPARING ACETYLENE AND SYNTHESIS GAS

CROSS-REFERENCE TO RELATED APPLICATIONS

This application claims the benefit of priority under Section 119(e) of U.S. Provisional application No. 61/412,406, filed Nov. 11, 2010, the contents of which are incorporated herein by reference.

The present application incorporates provisional U.S. application No. 61/412,406, filed Nov. 11, 2010, by reference.

BACKGROUND OF THE INVENTION

The present invention relates to an improved process for preparing acetylene and synthesis gas by partial oxidation of hydrocarbons in a reactor, in which a stream comprising the hydrocarbon and a stream comprising the oxygen are fed to the reactor, and to an apparatus for performing the process according to the invention.

High-temperature reactions for partial oxidation of hydrocarbons are typically performed in a reactor system composed of mixing unit, burner and quench unit.

One example of such a partial oxidation in the high-temperature range is the preparation of acetylene and synthesis gas by partial oxidation of hydrocarbons. This is described, for example, in DE 875198, DE 1051845, DE 1057094 and DE 4422815.

These documents explain the mixer/burner block/firing space/quench combinations typically used for the BASF-Sachsse-Bartholomé acetylene process—referred to hereinafter, when reference is being made to the combination, simply as "reactor".

In this process, the starting materials, for example natural gas and oxygen, are heated separately, typically up to 600° C. In a mixing zone, the reactants are mixed intensively and, after flowing through a burner block, reacted exothermically. In these cases, the burner block consists of a particular number of parallel channels in which the flow velocity of the ignitable oxygen/natural gas mixture is higher than the flame velocity (reaction rate, conversion rate), in order to prevent the flame from penetrating into the mixing space. The metallic burner block is cooled in order to withstand the thermal stresses. According to the residence time in the mixing space, the risk arises of premature ignition and reignition owing to the limited thermal stability of the mixtures. The term "ignition delay time" or "induction time" is used here as the period within which an ignitable mixture does not undergo any significant intrinsic thermal alteration. The induction time depends on the type of hydrocarbons used, the mixing state, pressure and temperature. It determines the maximum residence time of the reactants in the mixing space. Reactants such as hydrogen, liquefied gas or light petroleum, the use of which is particularly desirable owing to enhanced yield and/or capacity in the synthesis process, are notable for a comparatively high reactivity and hence short induction time.

The acetylene burners being used on the present production scale are notable for their cylindrical geometry in the firing space. The burner block preferably has hexagonally arranged passage bores. In one embodiment, for example, 127 bores of internal diameter 27 mm are arranged hexagonally on a circular base cross section with diameter approx. 500 mm. In general, the channel diameters used are of diameter about 19 to 27 mm. The downstream firing space in which the flame of the acetylene-forming partial oxidation reaction is stabilized is likewise of cylindrical cross section, is water-cooled and corresponds in terms of appearance to that of a short tube (for example of diameter 180 to 533 mm and of length 380 to 450 mm). At the height of the surface of the burner block on the firing space side, what is called auxiliary oxygen is supplied to the reaction space. This ensures flame stabilization and hence a defined distance of the flame root and hence of the commencement of reaction from the stoppage of reaction by the quench unit. The entire burner composed of burner block and firing space is hung from the top of a quench vessel of relatively large cross section by means of a flange. At the height of the exit plane from the firing space, outside the circumference thereof, quench nozzles are installed in one or more quench distributor rings, which atomize the quench medium, for example water or oil, with or without the aid of an atomization medium, and inject the reaction gases leaving the firing space approximately at right angles to the main flow direction. This direct quench has the task of cooling the reacting flow extremely rapidly to approx. 100° C. (water quench) and 200° C. (oil quench), such that further reactions, especially the degradation of acetylene formed, are frozen. The range and distribution of the quench jets is ideally such that a very substantially homogeneous thermal distribution is achieved within minimum time.

The acetylene burners used on the current production scale are notable for a cylindrical geometry of the firing space. The feedstocks are premixed by means of a diffuser and supplied, with avoidance of backmixing, to the burner block via passage bores in a hexagonal arrangement. In the known processes, the feedstocks are premixed in the mixing diffuser in a relatively large volume and with high preheating temperatures.

The industrial processes described form not only acetylene but essentially hydrogen, carbon monoxide and soot. The soot particles formed in the flame front can adhere as nuclei to the surface on the firing space side of the burner block, which then results in the growth, deposition and baking-on of coke layers, which adversely affects the effectiveness of the process.

In the existing production processes with oil and water quenching, these deposits are periodically removed by mechanical cleaning in the region of the surface on the firing space side of the burner block by means of a stoker unit. For this purpose, complex control of the stoker unit is necessary (Ullmann's Encyclopedia of Industrial Chemistry, 5th Edition, Volume A1, pages 97-144) and, in addition, the particular use time of the mechanism is limited by the thermal stress in the combustion space.

There has been no lack of attempts to avoid the disadvantage of the baking of coke layers onto the surface on the firing space side of the burner block. For instance, the teaching of DE 2307300 discloses the injection of a gaseous substance into the reactor in a region between maximum temperature and quenching site (claim 1). This is intended to lead to reactions between the gases added and free radicals, which is intended to reduce coke formation (description, page 8, second paragraph).

DE 3904330 A1 describes a process for preparing acetylene black by thermal decomposition of acetylene. It is mentioned in this process, which differs significantly from the process for preparing acetylene (e.g. no partial oxidation), that an inert gas stream is optionally introduced.

DE 1148229 describes a process for operating pyrolysis chambers for treatment of hydrocarbons, wherein purging with steam is provided and cooling of the wall is supposed to lead to a water curtain (claim 1). No further information is given about the way in which the purging is executed. The process presented is not a partial oxidation (POx), the purge medium introduced is liquid water, and additional admixing of an oxidizing agent (e.g. oxygen) with the purge medium is not provided. Furthermore, a purge medium is injected only at a maximum of one site in the axial profile of the pyrolysis chamber.

DE 2007997 describes how an oil film on the interior wall of the reaction chamber is supposed to prevent coking (page 2, first paragraph). However, an oil film in a firing space tends to coking per se. Therefore, a hydrocarbon-containing (mineral) oil can be ruled out as a purge medium given the present challenge.

The processes disclosed in the documents cited for prevention or reduction of unwanted coke formation, however, are unsatisfactory with respect to effective use in the process for preparing acetylene. For instance, some of the documents, as explained, relate to other reactions where the conditions are quite different and there is no applicability. For instance, the partial oxidation in the process according to the invention is very demanding in terms of characteristics: the residence times play a particularly major role, the stoppage of the reaction must be very exact, and the addition of extraneous substances, including, for example, a purge gas or oxidizer, can move the reaction very rapidly with respect to the site and also the rate thereof, thus leading to a yield loss.

In addition, the prior art contains only general statements, often in terms of the problem to be solved, about the technical configuration. Furthermore, the prior art contains explanations with respect to coking on the side surfaces which delimit the firing space, and not on the surface on the firing space side of the burner block, which is typically perpendicular to these side surfaces.

In addition, no geometry specifications in terms of flow mechanics and reaction technology are presented, on the basis of which the purge medium could be minimized effectively and hence operating costs could be minimized and product yield optimized.

It is thus an object of the present invention to find an improved process for partial oxidation of hydrocarbons, which suppresses baked-on and deposited material on the surface on the firing space side of the burner block in a simple manner in terms of process technology, in order that there is no need for mechanical cleaning of this surface on the firing space side of the burner block, and hence for periodic removal by means of mechanical stoker units which are subjected to high thermal stress and are difficult to control.

BRIEF SUMMARY OF THE INVENTION

Accordingly, a process has been found for preparing acetylene and synthesis gas by partial oxidation of hydrocarbons with oxygen, by first separately preheating the starting gases comprising a hydrocarbon-containing stream and an oxygen-containing stream and then mixing them in a mixing zone and, after they have flowed through the burner block, reacting them in the firing space and then cooling the products rapidly, wherein the surface on the firing space side of the burner block is covered with a purge gas stream and this purge gas stream is introduced through the burner block by means of several bores, where the averaged ratio of effective surface area of the burner block to number of these bores in the burner block for the purge gas stream is within a range from 5 to 100 $cm^2$.

The process according to the invention can be applied to commonly known processes for preparing acetylene and/or synthesis gas by partial oxidation. Suitable feedstocks among the hydrocarbons preferably include alkanes, alkenes, natural gases, light petroleum, and mixtures thereof with, for example, $CO_2$, synthesis gas. The oxygen-containing stream can be supplied, for example, via oxygen, or else mixtures comprising oxygen and, for example, $CO_2$, $H_2O$, $N_2$ and/or noble gases.

DETAILED DESCRIPTION OF THE INVENTION

Figure 1:
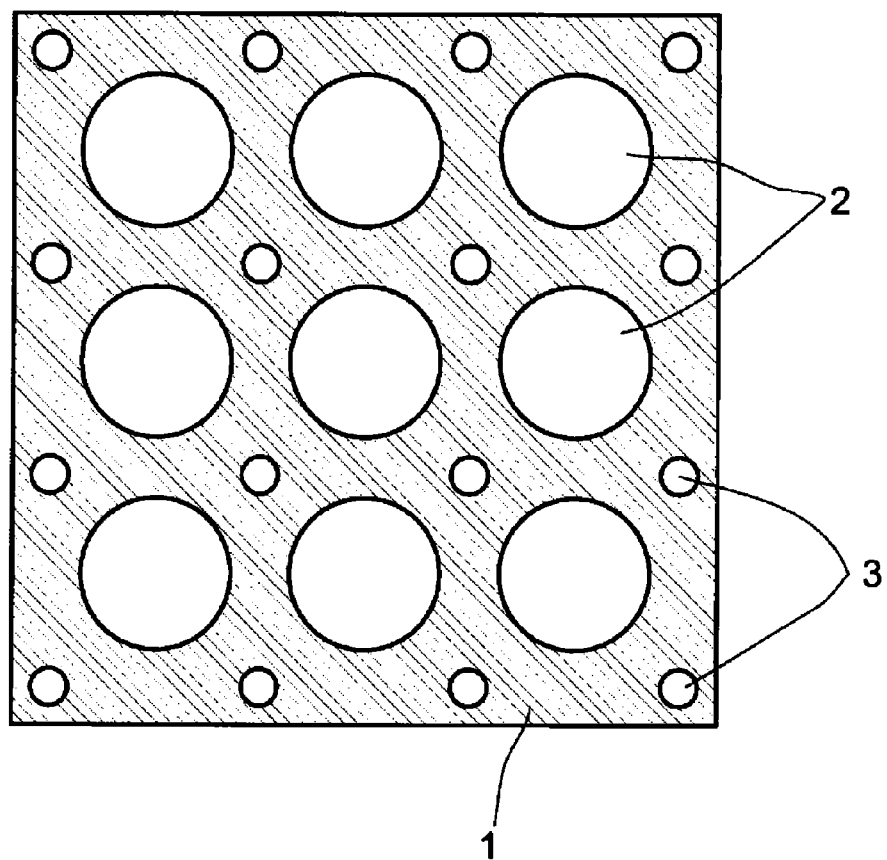
FIG. 1 is a schematic view of one embodiment of the inventive burner block, on the firing space side.

FIG. 1 shows a detail from the inventive burner. This shows the surface on the firing space side of the burner block (1) with two kinds of bores, which enable supply of streams into the firing space. Bores (2) are shown for the supply of the feedstock mixture, and bores (3) for the supply of the purge gas, the free cross section of the bores for the purge gas being kept smaller than that of the bores for the feedstock mixture. The bores are preferably circular cross sections, but it is also possible to employ other geometries. As can be inferred from FIG. 1, the number of bores for the purge gas in relation to an area segment being considered preferably exceeds the number of bores for the feedstock mixture.

With reference to FIG. 1, it is also possible to explain the term "effective surface area of the burner block". This is the hatched area shown here. It arises from the original surface area on the firing space side of the burner block, minus the parts of this area absent as a result of the bores for the feedstock mixture.

According to the invention, the number of bores (3) can vary in relation to a portion of the surface on the firing space side of the burner block. For example, it may be particularly advisable to provide, in the vicinity of the outer wall (i.e. the boundary wall of the firing space, which is generally at right angles to the surface of the burner block), a higher density of those bores (3) for the purge gas, in order to counter the undesired effect of coking in the vicinity of this relatively cold region where there is an increased risk of coke formation by enhanced supply of purge gas. In this case, the volume flow rate of the purge gas supplied in the edge region may preferably be 1.2 to 10 times the mean volume flow of purge gas (easily determinable by considering the mean of all purge gas feeds through all bores 3). Edge region is understood here to mean the outer approx. 10%-20% of the radial firing space dimension (in the case of circular cross sections this dimension corresponds to the diameter). In order to determine the "averaged ratio of effective surface area of the burner block and number of these bores in the burner block for the purge gas stream", an overall assessment is made. In this case, the ratio is formed from the total effective surface area (on the firing space side) of the burner block to the total number of bores for the purge medium. This averaged ratio is 5 to 100 $cm^2$, preferably 5 to 50 $cm^2$. As already outlined above, this ratio may vary over the surface area of the burner block.

The surface on the firing space side of the burner block, which is purged in accordance with the invention, thus comprises the effective surface area (on the firing space side) of the burner block minus the area proportions lost as a result of the bores for the purge gas. According to the invention, coking and growth of soot on this surface is prevented.

According to the invention, the purge gas stream used for this purpose is supplied through one or more feed lines to the corresponding bores in the burner block and exits at the surface on the firing space side of the burner block.

It is a significant aim of the process according to the invention to minimize the amount of the purge stream to be introduced in order to prevent significant deviation of the stoichiometry of the feedstocks, which would reduce the acetylene yield. In addition, the amount of the purge medium used should be reduced for reasons of economic viability. At the same time, high effectiveness should be maintained here in the prevention of the coking of the surface on the firing space side of the burner block. In order to achieve this effect, a very substantially homogeneous purge film should be ensured over the surface on the firing space side of the burner block. One example of a design solution can be found in FIG. 2. This again shows a detail from an inventive apparatus. This shows the surface on the firing space side of the burner block (1) with bores for the supply of the feedstock mixture (2) and bores for the supply of the purge gas (3). The ends of these bores (3), i.e. toward the firing space (6), are adjoined by a distributor device (4) for the purge gas. The arrows (5) indicate directions in which the purge gas is distributed.

In a preferred embodiment, large proportions of the purge gas added are conducted parallel to the surface on the firing space side of the burner block. An advisable proportion here is from 20 to 100% by volume, particularly 70 to 100% by volume. It may be particularly advisable here that the purge gas stream exiting from the distributor device is distributed radially in relation to the center axis of the feed line by a multitude of orifices arranged, preferably homogeneously, over the outer circumference of the distributor, which ensures a homogeneous (preferably parallel) distribution of the purge gas over the surface on the firing space side of the burner block. In this case, a distributor device preferably has at least three orifices for the exit of the purge gas, but there are typically significantly more orifices here in order to achieve good homogenization of the (radial) distribution. By virtue of this specific arrangement, the purge film directly and homogeneously adjoins the surface on the firing space side of the burner block which is to be purged, which is the most effective way of preventing penetration of soot particles to this wall. In addition, parallel outflow of the purge film with respect to the surface on the firing space side of the burner block which is to be purged transports incoming soot particles in the direction of the bores for the supply of the feedstock mixture, and they are converted in the flame which emerges there, which likewise promotes, in accordance with the invention, prevention of baking-on on the surface on the firing space side of the burner block.

In the addition of the purge gas, preferably 0.05 to 1 $m^3$ (STP) is added per hour and bore, more preferably 0.1 to 0.6 $m^3$ (STP) per hour and bore. These value ranges result firstly from the inventive specification of high exit speeds and hence high momenta of the purge medium (50-200 m/s), and secondly from the manufacturing specification of limited exit orifices (diameter approx. 0.1-1 mm), the economic demands of minimum amounts of purge medium, and the process-related specification of only minimum changes in the stoichiometry of the feedstocks. Under these preconditions, a density of purge bores of 5 to 100 $cm^2$ per bore has been found to be advisable.

In a preferred embodiment, the purge gas can be supplied in different amounts viewed over the overall effective surface area of the burner block, preference being given to supplying a higher amount in the vicinity of the boundary wall of the firing space. This allows soot deposition to be reduced further, since the tendency to coking is higher in relatively cooler regions such as in the vicinity of the boundary wall mentioned.

Different configurations are possible for the configuration of the distributor device (4). For example, it is possible to employ spherical, pyramidal, conical or cubic geometries. Pyramidal geometries, for example, may also be particularly advisable, in which case the tip is aligned in the direction of the firing space. By appropriate arrangement of small orifices in the distributor device, it is possible to introduce the purge gas correspondingly. The preferred requirement of the predominant parallel flow regime in relation to the surface of the burner block can be taken into account, for example, by an appropriate arrangement of these small orifices in the distributor device. In general, the dimensions of these small orifices should be kept to a minimum, also noting the given pressure of the purge gas.

Figure 2:
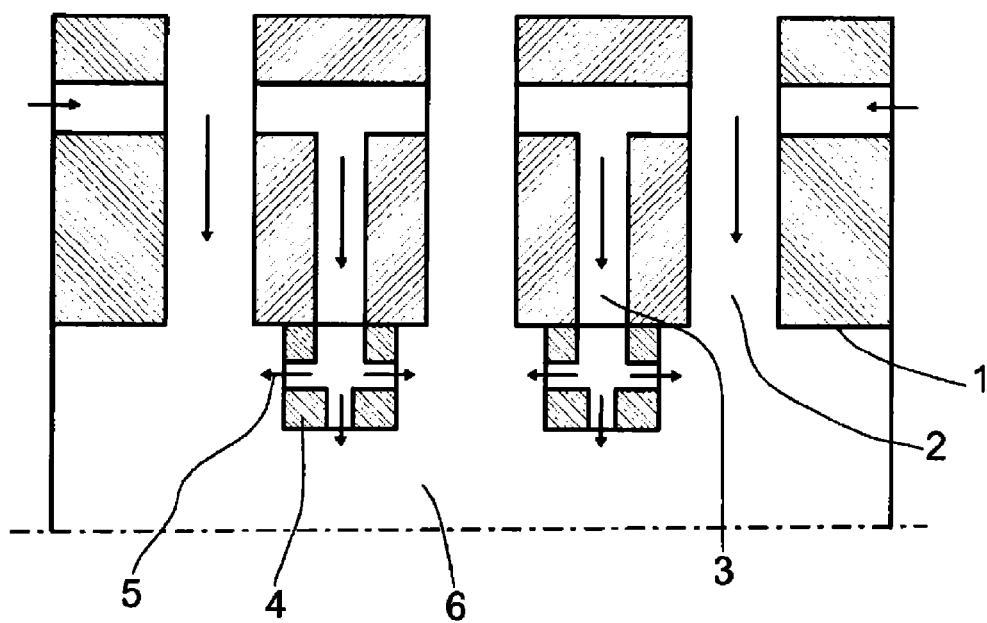
FIG. 2 is a schematic view of a cross section of one embodiment of the inventive burner block, showing a preferred embodiment of distributor devices for the purge gas.

According to the invention, a multitude of or all exit orifices from the distributor bodies (4) are in the immediate proximity of the surface of the burner block to be purged (as can be seen, for example, in FIG. 2).

In the process according to the invention, the desired purge principle may, according to the purge medium used, be based on two different mechanisms, both of which may also jointly come into effect, which gives rise to particular synergisms.

The first is pure pulsed, as described above, purging of the flow boundary layer. This leads to avoidance both of the penetration of solid coke/soot particles and the adhesion and growth of soot/coke layers. The velocity of the purge film over the purge surface (surface on the firing space side of the burner block) should preferably be as high as possible to prevent coke particles circulating out of the reaction zone from adhering to the surface.

Secondly, it is possible for the purge medium to create an oxidizing atmosphere close to the surface on the firing space side of the burner block, which prevents growth/adhesion of soot/coke by converting/combusting/oxidizing possible impurities with the aid of the oxidizer present in the purge medium, or slows the formation thereof to such an extent that formation of the solid phase is prevented for kinetic reasons.

According to the invention, any purge medium may be useful for production of the purge pulse, preferably oxygen. The temperatures of the purge medium are preferably below 500° C., more preferably within a range from 100 to 300° C. In this context, the temperatures mentioned relate to the entrance temperature of the purge medium into the firing space. In the case of the above-described oxidative purging action, preferred purge gases for given process technology boundary conditions are potentially oxidizing media, preferably steam, oxygen, $CO_2$, CO and mixtures thereof and of further inert components. The use of air as purge medium may also be advisable.

In a further preferred configuration of the process according to the invention, the interior wall of the firing space is additionally covered with a purge gas stream. This allows the overall effectiveness of the process to be enhanced further, since coking of this wall can thus also be countered effectively. Suitable purge media are essentially likewise the aforementioned feedstocks.

This invention further provides an apparatus suitable for the performance of the process according to the invention. This comprises a reactor comprising a burner block with a firing space for acetylene production, the burner block having bores for the supply of a purge gas stream for purging of the surface on the firing space side of the burner block, the averaged ratio of effective surface area of the burner block to number of these bores in the burner block for the purge gas stream being within a range from 5 to 100 cm$^2$.

The process according to the invention makes it possible to prevent encrustations on the surface on the firing space side of the burner block, which can avoid mechanical cleaning operations, for example the use of a stoker unit. It is thus ensured in a lasting manner that no troublesome solid particles of any relevant size get into the gas stream. This makes it possible, in a preferred configuration of the process according to the invention, to recover a large portion of the heat present in the gas after the reaction by means of a downstream heat exchanger. In this case, this energy obtained is preferably used to raise steam. Preferably, a majority of the heat for steam raising can thus be recovered from the product gas produced. Suitable heat exchangers are, for example, shell and tube heat exchangers. Preference is given here to cooling (quenching) the gas stream after the reaction, in contrast to the conventional process, not to 100° C. in the water quench or 200° C. in the oil quench, but rapidly to 600-1000° C. This does not yet lead to any significant yield losses of acetylene as a result of further reactions. Subsequently, this hot product gas is fed to a heat exchanger in which the gas is cooled further. The energy released is used for heat recovery. The heat exchanger is preferably a steam boiler in which the product gas is indirectly cooled further and steam is raised on the secondary side, which can then be used commercially or for operating purposes. This significantly enhances the effectiveness of the process. It is a significant advantage in the configuration of the process according to the invention that the heat exchanger can be connected directly downstream, since no solid deposits lead to problems in this case. In addition to use of the energy released in the cooling of the product gas for steam raising, there are also other opportunities to use this energy in the course of the process for preparing acetylene and synthesis gas.

Such a process regime is not achievable economically in the existing processes, since soot and coke slabs become detached from the surface on the firing space side of the burner block in the course of cleaning in the existing mechanical cleaning processes, are transported in the direction of the heat exchanger and damage it mechanically or abrasively or completely or partially block it. Compared to this, it is possible in accordance with the invention to completely suppress deposition of coke and soot on the surface on the firing space side of the burner block.

The process according to the invention gives an operatively simple and effective means of effectively reducing or even preventing encrustation and baking-on of coke on the surface on the firing space side of the burner block in the preparation of acetylene and/or synthesis gas by partial oxidation. By virtue of the inventive features outlined above, it is already possible here for a relatively small purge gas stream to effectively prevent encrustation, without any lasting impairment of the effectiveness of the reaction. In this case, in a preferred embodiment, the supply of the purge gas can advantageously be added in different amounts in individual regions of the surface on the firing space side of the burner block, which further increases the effectiveness. By appropriate selection of the purge medium, it is possible to create not only a "pure purge operation" based on a pulse of the purge stream, but optionally also preferably an oxidizing atmosphere, which can reduce the deposits further.

EXAMPLES

By way of example, the comparison between the operation of a burner block/firing space/quench for acetylene synthesis ("standard reactor") according to the prior art and the operation of a reactor with a burner block according to the invention is to be considered here.

Example 1

The standard reactor was operated for test purposes with conventional axial and radial flame stabilization. The firing space is configured with water cooling.

The reactor diameter with the burners used extends to 180 mm.

The burner block is configured with 19 bores of internal diameter 27 mm in hexagonal arrangement.

The standard reactor and all reactors mentioned hereinafter were operated under these reaction conditions:
natural gas volume flow rate: 600 m$^3$ (STP)/h
ratio of oxygen stream to natural gas stream=0.62
preheating temperature of the gases: 550° C.
acetylene in the volume: 6.4% by volume Under the given test conditions, the standard reactor had to be shut down after approx. 20 operating hours after the occurrence of flame stability problems.

On inspection of the surface on the firing space side of the burner block, a coke layer of several centimeters in thickness which had developed on the surface on the firing space side of the burner block can be found in the standard reactor.

The growth rate of the coke layer on the surface on the firing space side of the burner block can be determined to be 2 mm/h.

Example 2

For comparison, an inventive reactor with a burner block was used, wherein the burner block was covered with a purge gas stream, where the averaged ratio of effective surface area of the burner block to number of bores in the burner block for the purge gas stream was 7 cm$^2$. 90% of the purge gas stream was supplied by means of distributor devices parallel to the surface on the firing space side of the burner block and radially in relation to the center axis of the bores in the burner block for the feeding of the purge gas stream. In accordance with the invention, the purge gas stream consisted of oxygen.

In the course of operation of the inventive reactor with a burner block, there are no deposits on the surface on the firing space side of the burner block over an operating time of 20 h. The growth rate of the coke layer on the surface on the firing space side of the burner block is accordingly 0 mm/h.

The invention claimed is:

1. A process for preparing acetylene and synthesis gas, the process comprising:
    first, separately preheating starting gases comprising a hydrocarbon-comprising stream and an oxygen-comprising stream; then
    mixing the starting gases in a mixing zone to form a mixture of starting gases;
    passing the mixture of starting gases through a burner block;
    after the mixture of starting gases have flowed through the burner block, reacting the mixture of starting gases in a firing space, to form products; and then
    cooling the products rapidly,
    wherein:
        a surface on a firing space side of the burner block is covered with a purge gas stream which is introduced through the burner block by two or more purge gas bores;

an averaged ratio of effective surface area of the burner block to a number of the purge gas bores in the burner block is within a range from 5 to 100 cm$^2$; and the purge gas stream conducted through the purge gas bores is deflected by at least one distributor device such that 70 to 100% by volume of the purge gas stream is conducted parallel to the surface on the firing space side of the burner block.

2. The process according to claim 1, wherein the averaged ratio of effective surface area of the burner block to number of the purge gas bores in the burner block for the purge gas stream is within a range from 5 to 50 cm$^2$.

3. The process according to claim 1, wherein a purge gas stream exiting from the distributor device is distributed radially in relation to a center axis of a feed line supplying the purge gas stream to the purge gas bores.

4. The process according to claim 1, wherein the purge gas stream is supplied in different amounts over an overall effective surface area of the burner block, such that a higher amount is supplied in a vicinity of a boundary wall of the firing space.

5. The process according to claim 1, wherein a purge medium of the purge gas stream is steam, oxygen, or a mixture thereof.

6. The process according to claim 1, wherein a boundary wall of the firing space is also covered by a purge gas stream.

7. The process according to claim 1, wherein acetylene and synthesis gas are formed by partial oxidation of at least one hydrocarbon.

8. The process according to claim 1, wherein a purge medium of the purge gas stream consists of oxygen.

* * * * *